United States Patent [19]
Steer

[11] 3,973,565
[45] Aug. 10, 1976

[54] WINGED CANNULA WITH SKIN SECURING MEANS

[75] Inventor: Peter Steer, East Grindstead, England

[73] Assignee: Everett Medical Products Limited, England

[22] Filed: July 5, 1974

[21] Appl. No.: 486,235

[30] Foreign Application Priority Data
July 20, 1973 United Kingdom............... 34720/73
May 2, 1974 United Kingdom............... 19258/74

[52] U.S. Cl...................... 128/214.4; 128/DIG. 26; 128/348
[51] Int. Cl.² ......................................... A61M 5/00
[58] Field of Search............. 128/133, 214 R, 214.4, 128/221, 348, DIG. 26

[56] References Cited
UNITED STATES PATENTS

| | | | |
|---|---|---|---|
| 2,821,194 | 1/1958 | Simmons.......................... | 128/214 R |
| 3,064,648 | 11/1962 | Bujan.............................. | 128/214 R |
| 3,138,158 | 6/1964 | Gordon et al...................... | 128/133 |
| 3,670,727 | 6/1972 | Reiterman....................... | 128/214 R |
| 3,782,383 | 1/1974 | Thompson et al.............. | 128/214 R |
| 3,863,631 | 2/1975 | Baldwin........................... | 128/214 R |

*Primary Examiner*—Dalton L. Truluck
*Attorney, Agent, or Firm*—Brisebois & Kruger

[57] ABSTRACT

A surgical device of the kind having a cannula fitted with a laterally extending wing or wings also includes a sheet of flexible material having an adhesive surface which is fixed to the wing or wings and is capable of folding forwardly beyond the wing or wings to engage the skin of the patient to hold both the cannula and the remainder of the device in position. This avoids the need for the separate piece of surgical plaster used in the past since the adhesive-covered flexible sheet is automatically to hand and is automatically located with considerable accuracy. With a double wing construction the flexible sheet is preferably fixed so as to extend from the rear edge of the wings and when folded forwardly this brings the layer of adhesive into contact with the upper surface of the wings and also into contact with the skin of the patient beyond the forward edge of the wings. The sheet of flexible material preferably carries a layer of pressure-sensitive adhesive covered by a removable barrier sheet.

22 Claims, 11 Drawing Figures

WINGED CANNULA WITH SKIN SECURING MEANS

This invention relates to surgical devices including a cannula for insertion in the tissues or a body cavity of a patient for the introduction or removal of fluids. Such devices are most commonly intended for intravascular use, particularly for infusion purposes, although various other uses are quite common, such as drainage tubes and so forth. After insertion in the body of a patient the cannula is generally connected by a length of tubing to a container for the fluid which is to be introduced or withdrawn. Since the cannula will normally need to be left in position for at least several hours, it needs to be attached to the body of the patient and in order to assist in the initial manipulation and subsequent attachment of the cannula in position, the cannula may be fitted with a laterally extending wing or wings.

When there are two such wings, they extend in opposite directions and are capable of being folded axially into a position in which they extend side-by-side to form a handle for the cannula so as to assist the initial insertion and may then be folded flat against the body of the patient to assist in attachment, e.g. by a piece of surgical plaster applied over the wings and cannula. With only a single wing, this extends outwardly during insertion and is then turned to a position in which it lies flat against the body, by rotation of the device as a whole, including the cannula. The single wing needs to be held in position as mentioned above, i.e. with a piece of surgical plaster. Whether there are two wings or one, it is important that the piece of plaster used should be fitted accurately in position, but the manipulation is somewhat difficult since the device as a whole must be held firmly in position at the same time.

According to the present invention, a surgical device comprising a cannula fitted with a laterally extending wing or wings as just described has a sheet of flexible material fixed to the wing or wings, this sheet having an adhesive surface and being capable of folding to engage the skin of the patient to hold both the cannula and the remainder of the device in position. In other words, the adhesive-covered flexible sheet takes the place of the separate piece of surgical plaster used in the past, but since it is fixed to the device itself, it is automatically handy and is easily located with considerable accuracy when folded it preferably engages the skin so as to cover the exposed portion of the cannula, i.e. the portion extending between the wing or wings and the point of entry into the patient. If the cannula penetrates the skin of the patient, the flexible sheet may also, if desired, cover the wound, that is to say the point of insertion of the cannula into the skin of the patient. Thus the device as a whole is attached firmly and accurately to the patient and the wound is effectively covered and protected from risk of contact or infection.

With a double wing construction the flexible sheet is preferably fixed so as to extend from the rear edge of the wings, that is to say the edge remote from the insertion point of the cannula. Prior to insertion, the flexible sheet then extends in the plane of the wings in a direction away from the point of insertion of the cannula. When the wings are folded together to form a handle, the flexible sheet folds with them and when the wings are then folded flat against the skin of the patient the flexible sheet does likewise. The adhesive-covered side is then facing upwardly and when the sheet is folded forwardly this brings the layer of adhesive into contact with the upper surfaces of the wings and also into contact with the skin of the patient beyond the forward edge of the wings, while also, if desired, covering the wound, if there is one. The flexible sheet is preferably wider than the wings so that when folded forwardly in this way, it also engages the skin of the patient beyond the outer ends of the wings so as to assist in holding these firmly against the patient's skin.

Generally speaking, the sheet of flexible material may carry a layer of pressure-sensitive adhesive covered by a removable barrier sheet. This barrier sheet remains in position while the cannula is inserted into the patient and when the wing or wings and flexible sheet have then been folded flat against the skin, it is a simple matter to hold the device in position with one hand and to peel off barrier sheet with the other hand while the flexible sheet is being folded forwardly as already described.

In its simplest form, the flexible sheet may be generally rectangular in shape. When folded forwardly, this covers the wing or wings and also a rectangular area on either side of the cannula. When the device is eventually to be removed from the patient, the sheet needs to be peeled off from the skin of the patient and it is usually simplest to start the peeling operation at one corner. This tends to produce a slight lateral force on the cannula and to avoid this, it is preferable to start first at one corner and then at the opposite corner and then to peel the sheet directly along the line of the cannula. This operation is considerably simplified if the flexible sheet is shaped so as to taper symmetrically towards its free end from the region intended to cover the wing or wings. This defines a relatively narrow area at the free end of the sheet, at which the peeling operation may be started and which then enables the sheet to be pulled away from the skin by means of a direct pull along the line of the cannula and without the need for making a separate start at each of two corners. The operation may be still further simplified if the surface of the free end of the sheet in the region of the narrow area just mentioned is nonadhesive. This small area is thus left free and may readily be grasped between the thumb and forefinger to assist in the peeling of the sheet.

Whatever the shape of the flexible sheet, it is desirable that an area of the skin in the region of the location of the end of the cannula should be left exposed. If, for example, the skin becomes distended locally as a result of extravasation, this may then readily be observed. If the flexible sheet terminates a short distance beyond the end of the cannula, a small recess may be formed in the end of the sheet for this purpose, whereas if the sheet is longer than this, an opening in the sheet may be necessary.

As mentioned previously, the cannula may take the form of a wide variety of tubes used for surgical purposes. If it needs to penetrate the skin and tissues of a patient it will generally take the form of a needle with a pointed end and may be of metal or hard plastics material. Particularly if the cannula is to remain in position for a long period of time, it is more comfortable for the patient if the cannula is made of relatively soft plastics material, in which case it may not be sufficiently sharp for introduction directly through the skin of a patient. The device then needs to include a removable introducer needle fitted in the cannula and having a mount engaging the mount of the cannula so that the two are held together. The introducer needle needs to project slightly beyond the end of the cannula so that shortly after the introducer needle has pierced the skin of the patient the cannula itself passes through the same perforation and, once the cannula itself is in position, the introducer needle can then be removed by disengaging the two mounts. After the removable of the introducer needle, an alternative connection is then made to the mount of the cannula.

One method of producing a surgical device having a cannula and a laterally extending wing or wings is by an injection moulding process which involves locating the cannula in a die and injecting plastics material constituting the wing or wings around the cannula. Not only is this a time-consuming process, but difficulty is experienced in obtaining an effective bond between the material of the wing or wings and the cannula, particularly when the cannula is in the form of a metal needle. A device in accordance with the present invention lends itself to a considerably simpler form of construction and method of production. For this purpose, the wings are formed from two layers of plastics material secured together face-to-face with a length of the cannula between them. For a single wing, a single sheet may pass around the cannula and be folded back on itself and be secured, but with two wings it is more convenient to use two separate sheets. In other words, the cannula is effectively sandwiched between the two sheets of plastics material.

The cannula may project from one end of a length of flexible tubing which may either be quite short, being formed with a mount immediately to the rear of the wing or wings, or may be considerably longer. The securing together of the two layers of plastics material effectively unites them to the material of the tubing surrounding the cannula and the formation of a bond under pressure fixed the cannula firmly in position. The two layers of plastics material are most conveniently secured together by a welding operation, part of the sheet of flexible material being inserted between the plastics sheets prior to welding so that the flexible sheet is fixed to the wings by the welding operation. The welding may conveniently be carried out by means of radio frequency heating which leads to a particularly simple and convenient manufacturing process, which has many advantages over injection moulding. In order to assist the fixing of the flexible sheet in position, this may be formed with tongues each having a cut-out portion to assist in anchoring, these tongues being inserted between the plastics sheets prior to welding. When the weld is made, the plastics sheets are welded together through the cut-outs in the tongues, e.g. holes or slots, thus firmly anchoring the sheet of flexible material in position.

It is by no means essential that the flexible sheet should be fixed in this way, or even that it should be fixed during the manufacture of the remainder of the device. All that is necessary is that it should be fixed by the time the device is to be used and the actual fixing may be carried out immediately prior to use. Thus the wing or wings and the flexible sheet may be fitted with cooperating portions of an attachment device or the sheet may be so constructed as to be capable of removable fixing to an otherwise standard wing or wings, e.g. by means of pressure-sensitive adhesive. In particular, if the flexible sheet has a layer of pressure-sensitive adhesive for attachment to the skin of a patient, a portion of the same layer may be continued over a portion of the sheet intended for attachment to the wing or wings of the device, separate barrier sheets being fitted to the two portions of the layer. One barrier sheet is removed first to enable the sheet to be fixed to the device and the other subsequently, during use, as previously described.

When intended for use with a standard device, the flexible sheet may be supplied separately and used as required. The characteristics of such a sheet are a main body portion provided with a layer of pressure-sensitive adhesive and a barrier sheet, and a pair of spaced tongues for attachment to the wing or wings of a surgical device. The tongues may have a layer of pressure-sensitive adhesive and a barrier sheet, as previously mentioned, and, in order to increase the area of attachment, the tongues may be connected together by a cross-member to leave a small inspection opening, through which tubing attached to the cannula of the device may be observed.

Constructions of device in accordance with the invention together with their mode of use and method of manufacture will now be described in more detail, by way of example, with reference to the accompanying drawings, in which.

Figures 1, 2:
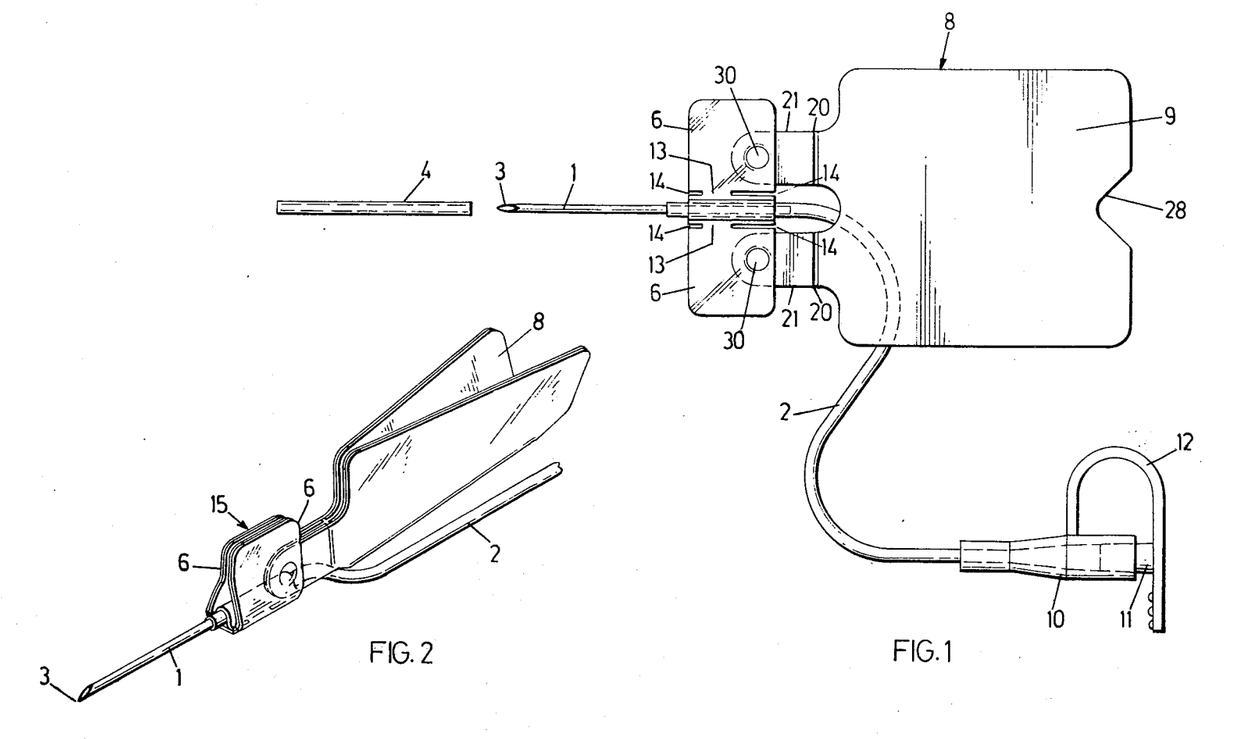
FIG. 1 is a plane view of one form of device in which the cannula is in the form of a metal needle.
FIG. 2 is a perspective view of the device in condition ready for insertion into the patient.

Turning first to FIG. 1, the device comprises a cannula in the form of a metal needle 1 projecting froom one end of a length of flexible tubing 2. The needle is formed at 3 with an oblique point fitted with a tubular protector 4 shown removed in FIG. 1. The device includes a pair of laterally extending wings 6 connected to the body of the device by narrow portions 13 defined by slits 14 which cause a more favourable redistribution of forces applied to the needle 1 by way of the wings 6. A sheet of flexible material 8 is fixed to the wings 6 so as to extend from their rear edges. The upper surface of this sheet includes a layer of pressure-sensitive adhesive covered by a barrier sheet 9 best seen in FIG. 3 which shows it in the process of removal to reveal the pressure-sensitive adhesive shown as 10. The end of the tubing 2 remote from the needle 1 is fitted with a Luer mount 10 closed by a captive plug 11 held by a flexible strip 12. When the plug 11 is removed, as shown in FIG. 4, the mount 10 allows the tubing to be connected to a further length of tubing leading to a container.

As seen in FIG. 1, the device is flat and, in this condition, can readily be packaged and stored. FIG. 2 shows the device ready for use, with the needle protector 4 removed and the wings 6 folded about axially-extending fold-lines so as to extend side-by-side to form a handle indicated generally as 15. Since the sheet 8 is also flexible, it folds into the configuration shown in FIG. 2 and thus does not impede the folding of the wings 6, although this sheet forms no part of the handle 15. It will be noted that in this position, the bevel is uppermost and the point 3 is lowermost, i.e. in the correct position for insertion into a patient.

Figure 3:
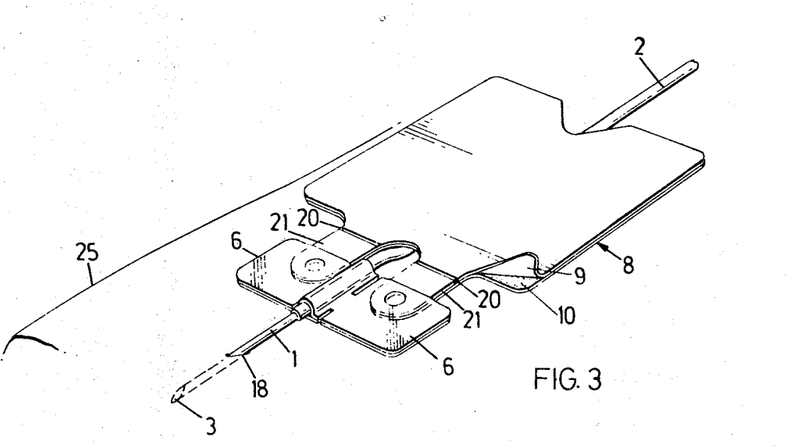
FIG. 3 is a perspective view showing the device after insertion into a patient and with a barrier sheet partially peeled.

FIG. 3 shows the device after insertion into the patient, with the point 3 located within the tissue of the patient, commonly in a vein, the needle having made a small perforation or wound indicated as 18. The wings 6 are shown as having been released so as to return to their original flat configuration and the flexible sheet 8 has returned to a similar configuration with the layer of adhesive 10 uppermost. While in this position it is a relatively simple matter to peel off the barrier sheet 9 as indicated so as to expose the layer of adhesive, the barrier sheet terminating at lines 20 on tongues 21 by means of which the sheet 8 is secured to the wings 6. As the barrier sheet 9 is removed, the sheet 8 may be folded forwardly about the lines 20 so that the adhesive 10 is facing downwardly for attachment to the skin of the patient which is indicated as 25 in FIGS. 3 and 4.

Figure 4:
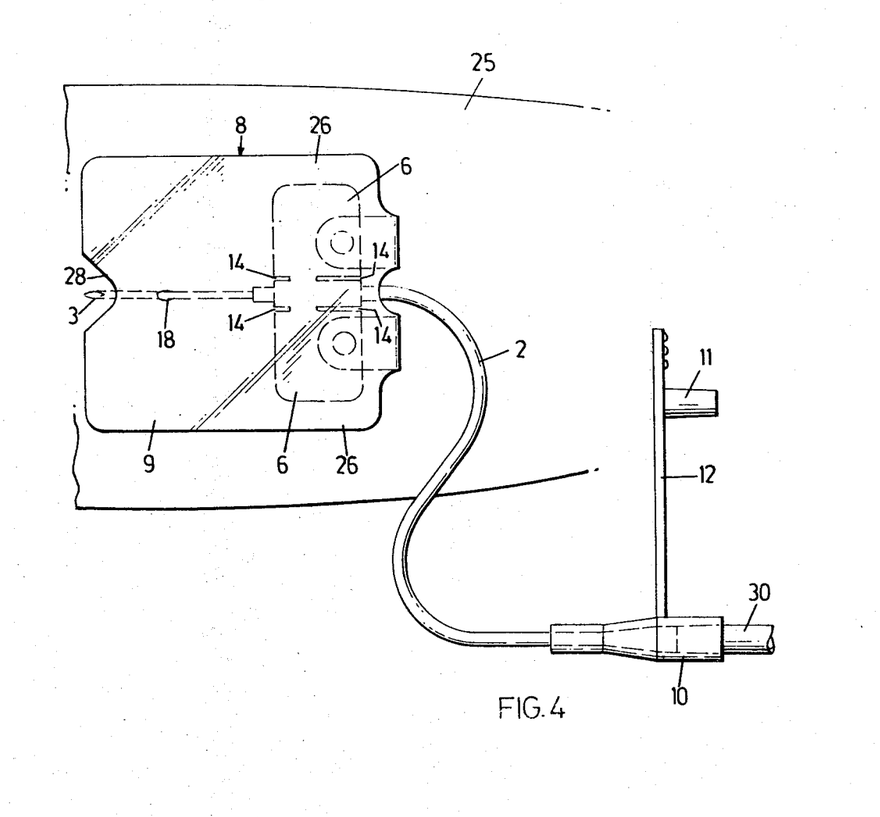
FIG. 4 is a plan view similar to FIG. 1, but showing the device attached to the skin of the patient at one stage later in the operation than FIG. 3.

This position is indicated in FIG. 4 which shows the sheet 8 in adhesive contact with the skin 25. It will be seen that the sheet 8 completely covers the wings 6 and since it is wider than the wings, it extends beyond their outermost ends at 26 so as to hold the wings firmly in position. In addition, and more importantly, the sheet 8 extends over the portion of the needle 1 projecting beyond the wings 6 so as to cover the whole of the needle lying outside the tissues of the patient and also to cover the perforation or wound 18, thus protecting it from dirt and infection. A notch 28 formed in the end of the flexible sheet 8 serves as an indication of the location of the point 3 within the tissues of the patient, leaving the location uncovered for purposes of observation. As previously mentioned, the plug 11 is shown withdrawn from the mount 10 which is connected to a further length of tubing 30 leading to a container which may either supply liquid to be infused or alternatively may receive fluid withdrawn or drained from the body of the patient.

Figure 5:
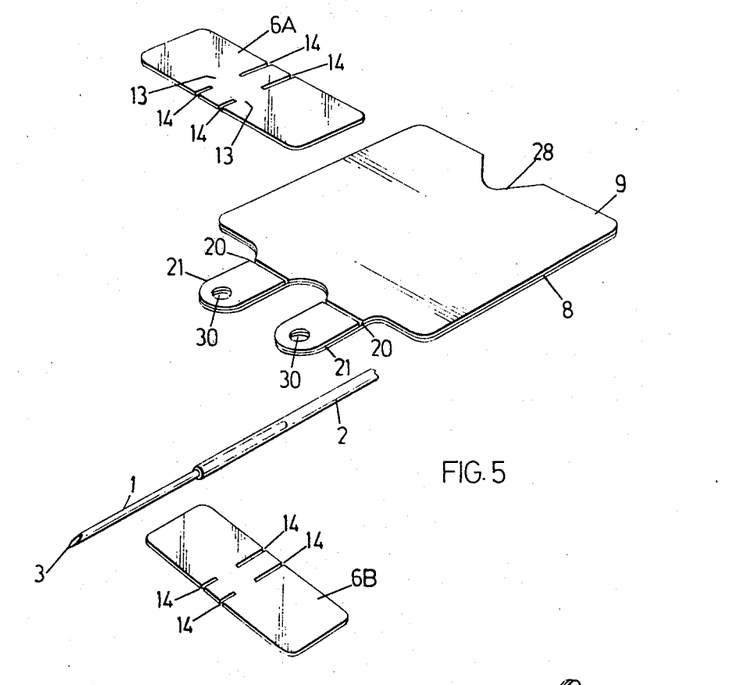
FIG. 5 is an exploded view of the same device showing the separate components.

FIG. 5 illustrates the components of the device in exploded form which facilitates description of the method of manufacture. It will be seen that the wings 6 are formed from two identical sheets of plastics material shown as 6A and 6B which are assembled on either side of the length of tubing 2 in the region where the tubing contains the rear end of the needle 1, shown in dotted lines. The tongues 21 extending from the flexible sheet 8 are each formed with a circular hole 30 and when the components are assembled together, the parts of the tongues 21 including the holes 30 are inserted between the sheets 6A and 6B in the position seen in FIG. 1, for example. The components are all brought together in a jig so that the end portion of the tubing 2 and the two tongues 21 are tightly sandwiched between the sheets 6A and 6B. While held in this position, the two sheets 6A and 6B are welded together, thus constituting the wings 6 and anchoring the end of the tubing 2, and hence the end of the needle 1, and also the tongues 21 firmly in position. The presence of the holes 30 in the tongues 21 allows a weld to be made through these holes, thus constituting the equivalent of plastics rivets holding the tongues in position. The sheets 6A and 6B and the tubing 2 are preferably made of plasticised polyvinyl chloride which is particularly suitable for a welding process such as by radio frequency heating and is also particularly suitable for surgical purposes. The flexible sheet 8, which serves as the equivalent of a piece of surgical plaster is coated with hypoallergenic adhesive with a barrier sheet 9 made of release-coated paper.

In order that the point of the needle 1 can be inserted into the patient with accuracy and certainty, it is important that the actual point 3 should be lowermost, i.e. with the bevel uppermost, as illustrated in all the Figures of the drawings. Once the needle 1 has been located in the jig, it is anchored firmly between the sheets 6A and 6B without the possibility of rotation. In this respect and also in respect of the overall simplicity, the method of assembly just described is greatly superior to the injection moulding process previously used for devices of this general kind, that is to say comprising a cannula fitted with laterally extending wings. Even though the needle 1 is held firmly by the wings 6, a small degree of angular rotation would still be possible if the wings 6 were to be folded upwardly in an unsymmetrical manner, i.e. with one wing projecting upwardly further than the other. FIG. 2 shows the wings folded symmetrically with their outer ends in accurate alignment, and this condition is assisted by the formation of surface irregularities on the upper surfaces of the wings. Details of these irregularities are not illustrated in the drawings, but they may be constituted for example merely by surface roughening of the upper surfaces of the wings or by small cooperating projections and depressions. The presence of these irregularities ensures that when the wings are folded upwardly and gripped together, there is no risk of relative slipping with consequent rotation of the needle 1.

Figure 6:
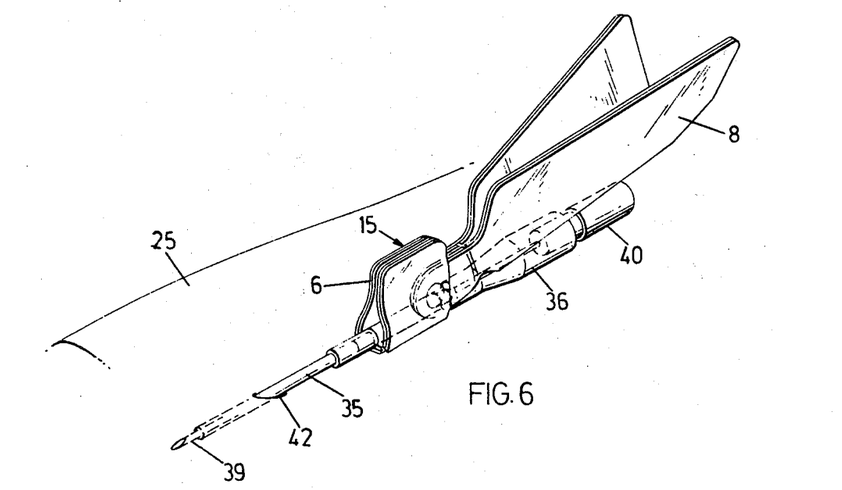
FIG. 6 is a perspective view of an alternative form of device including a cannula of plastics material and an introducer needle, after insertion in a patient.
Figure 7:
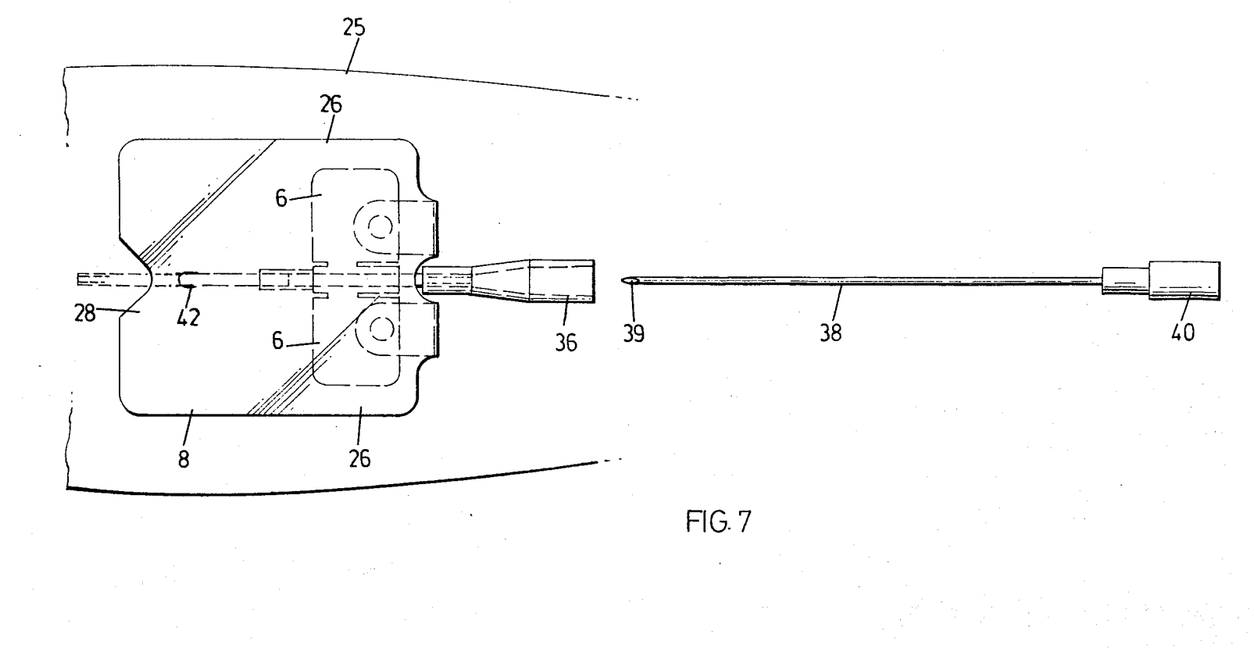
FIG. 7 is a plan view of the device shown in FIG. 6 after attachment to the patient and removal of the introducer needle.

FIGS. 6 and 7 show an alternative form of device in accordance with the invention in which the assembly of the wings 6 and the flexible sheet 8 is identical with that already described, the parts being indicated by the same reference numerals, but the cannula, instead of being a metal needle is in the form of a plastics tube 35 having a Luer mount 36 at its rear end and fitted with a removable introducer needle 38, of which only the point 39 and mount 40 are visible in FIG. 6. The mount 40 locks into the mount 36 during use so that the point 39 projects beyond the end of the cannula 35 in penetrating the skin 25 of the patient at 42, the cannula 35 following the introducer needle 38 into the perforation thus made. FIG. 6 shows the device in condition ready for use, i.e. corresponding to FIG. 2 and the operation of insertion is substantially the same as already described with reference to FIG. 2. After insertion, the wings 6 and flexible sheet 8 are folded flat, the barrier sheet 9 is removed and the sheet 8 is folded forwardly as illustrated in FIG. 7 so as to cover both the wings 6, the portion of the cannula 35 lying outside the body of the patient and, most importantly, the wound or perforation 42. As with the previous construction, the notch 28 indicates the approximate site of the end of the cannula 35.

Once the device has been attached firmly in position to the skin 25 as just described, the introducer needle 38 is withdrawn as illustrated in FIG. 7. The mount 36 is then available for connection to a further length of tubing such as that illustrated as 30 in FIG. 4 and thereafter the operation is the same as already described with reference to FIGS. 1 to 4 except that the portion of the cannula embedded in the patient is of relatively soft plastics material instead of rigid metal and thus causes less discomfort if it is to be left in position for long periods.

Figure 8:
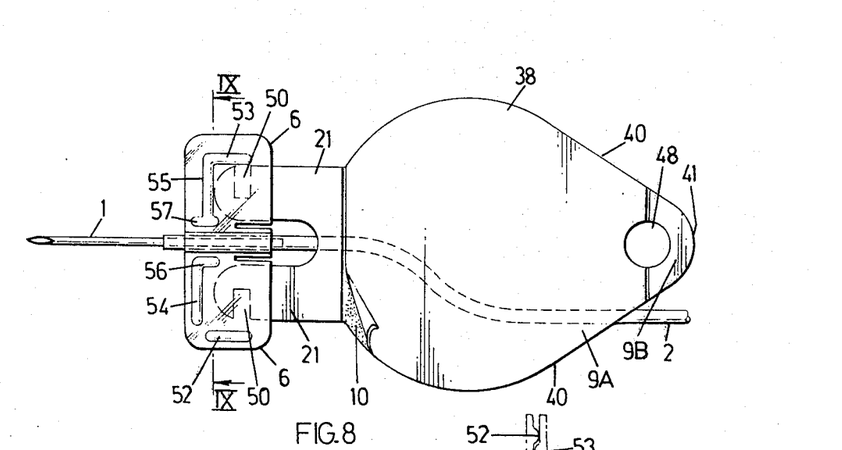
FIG. 8 is a view similar to that of FIG. 1 of a modified construction.
Figures 9, 10:
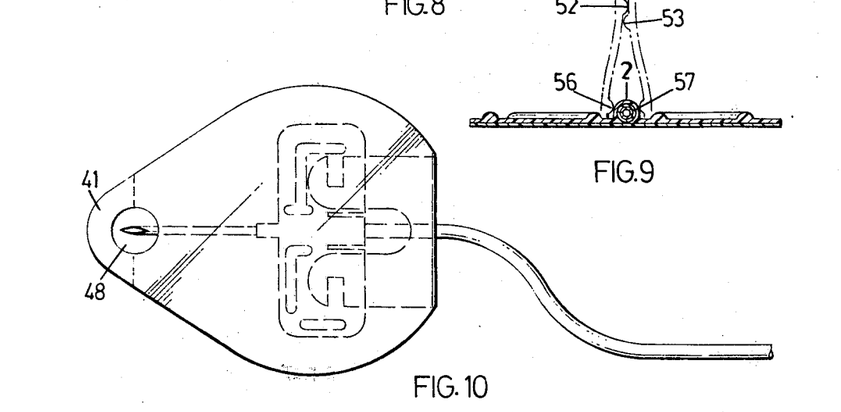
FIG. 9 is a cross-section on the line IX—IX in FIG. 8.
FIG. 10 is a view similar to that of FIG. 4 of the device of FIG. 8.

FIGS. 8 to 10 illustrate a construction which is the same in principle as that of FIGS. 1 to 5, but with modifications both to the adhesive flexible sheet and to the wings. Again, parts corresponding to those shown in FIGS. 1 to 5 are indicated by the same reference numerals. In these Figures the flexible sheet is shown as 38 and instead of being substantially rectangular as in the earlier Figures, is approximately pear-shaped, tapering symmetrically towards its free end as indicated at 40. Thus, although the sheet is wide enough to cover the wings 6, its free end shown as 41 is relatively narrow, which considerably facilitates the peeling of the sheet when the device is to be removed from the patient. The overall length of the sheet is slightly greater than that shown in the earlier Figures and, instead of a notch 28, an opening 48 is provided in order to expose the location of the point of the needle, as indicated in FIG. 10.

The pressure-sensitive adhesive shown as 10 is again covered by means of a barrier sheet, but this is made in two separate portions shown as 9A and 9B. The main portion 9A is peeled as the sheet 38 is folded forwardly and pressed against the skin of the patient. The portion 9B, on the other hand, is left in position so that the free end of the sheet is non-adhesive. Accordingly, when it is required to strip the sheet from the skin of the patient, the free end 41 constitutes a tab which can readily be grasped and which enables the sheet as a whole to be stripped by means of a direct pull along the line of the needle 1.

A further minor modification to the sheet 40 is that the tongues 21, instead of having circular holes 30 as shown in FIG. 1, are formed with cutaway portions in the form of notches 50. These serve the same function as the holes 30 in anchoring or keying the tongues 21 in position between the two sheets making up the wings 6 when these are welded together during the manufacturing operation.

As described with reference to the earlier Figures, the engaging surface of the wings 6 are formed with surface irregularities not shown in the drawings. In FIGS. 8 to 10, these irregularities take the form of projecting ribs on the upper surfaces of the wings 6. When the wings are folded together to form a handle as shown by the dotted line position of FIG. 9, these ribs lie alongside one another so as to prevent relative displacement of the wings 6. There are two main longitudinal ribs 52 and 53, the rib 52 being slightly closer to the outer edge of the respective wings 6 than the rib 53. Accordingly, when the wings are folded upwardly to the dotted line position of FIG. 9, the two ribs lie alongside one another to assist in preventing relative displacement of the two wings. Transverse ribs 54 and 55 (not seen in the dotted line position of FIG. 9) also lie alongside one another when the ribs are folded together and assist in preventing relative displacement of the two wings in the longitudinal or axial direction. Subsidiary longitudinal ribs 56 and 57 abut against the tubing 2 extending from the needle 1 when the wings are folded and thus further assist in symmetrical folding of the two wings.

Figure 11:
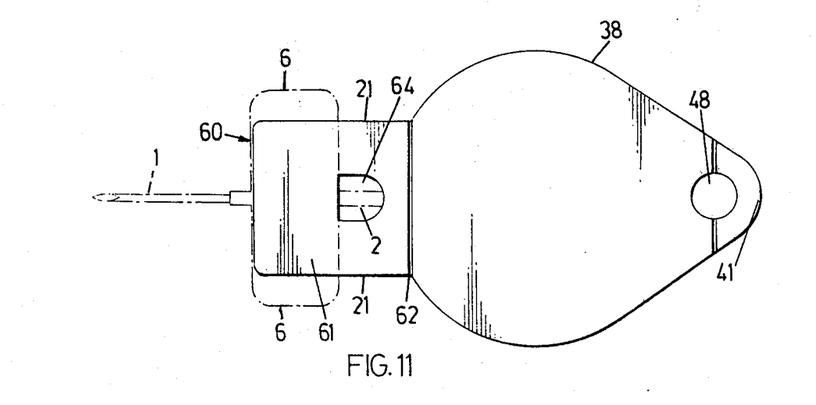
FIG. 11 is a view similar to that of FIG. 8 of a further modification.

FIG. 11 shows a further form of construction in which the flexible adhesive sheet 38 is basically the same shape as in FIGS. 8 to 10, but is removably fixed to the wings of the device. Since the main novelty in this Figure lies in the flexible sheet itself, the remainder of the device is shown only in dotted outline and the parts are indicated by the same reference numerals as previously. The sheet is seen from its upper side, that is to say the side facing away from the skin of the patient in operation. The main body of the sheet is of the same shape as in FIG. 8 and needs no further description. Thus it includes a non-adhesive portion 41 and an opening 48 in the locality of the point of the needle 1. The major difference is that the layer 10 of pressure-sensitive adhesive extends over the tongues 21, these tongues being interconnected by a cross-member 60. The sheet 38 is supplied separately and is fixed to the wings 6 in advance of the time when it is to be used so that the fixing of the sheet 38 forms no part in the sequence of steps during operation and, from a practical point of view, the complete device may be used in exactly the same way as the constructions previously described.

In fixing the sheet 38 to the wings 6, a portion of the barrier sheet shown as 61 is first removed and the adhesive thus exposed is pressed against the underside of the wings 6. Thus, as shown in FIG. 11, the wings 6 are on top of the cross-member 60 and the adhesive is facing upwardly, as it is on the remainder of the sheet 38. Consequently, when the remainder of the barrier sheet is peeled away in the same way as illustrated in FIG. 3, the sheet 38 may be folded forwardly about a line shown as 62 so as to cover both the wings and the needle 1 in the same manner as previously described. Although the wings 21 are interconnected by the cross-member 60, an inspection opening 64 is left, through which the tubing 2 extending from the needle 1 can be seen. Generally speaking, this tubing will be transparent and when the needle 1 is inserted in a vein for the withdrawal of blood, it is important that the blood should be visible in the tube 2 so as to ensure that the needle 1 is in the correct location. A similar opening is, of course, provided automatically inn all the other constructions as a result of the space between the tongues 21.

Whether the flexible adhesive sheet is incorporated as part of the device during manufacture or whether it is supplied separately and fixed in position prior to use, the advantages are the same in that the sheet is automatically to hand during use and automatically in the correct position for securing the device as a whole firmly and accurately in position and, at the same time, covering the wound, if any.

I claim:

1. In a surgical device of the kind comprising a cannula fitted with at least one laterally extending flexible, flattened wing permanently attached thereto, the improvement which comprises an additional sheet of flexible material having an adhesive surface, said sheet being connected to said at least one wing and being of a size so as to be capable of folding over said at least one wing to first cover said wing and thereafter engage the skin of a patient whereby to hold said device in position.

2. A surgical device according to claim 1 and having a pair of laterally extending wings, in which said sheet of flexible material extends from the rear edge of said wings, whereby when folded forwardly said sheet covers said wings and extends beyond the forward edge of said wings to engage the skin.

3. A surgical device according to claim 1, in which said adhesive surface of said sheet of flexible material comprises a layer of pressure-sensitive adhesive and including a removable barrier sheet covering said pressure-sensitive adhesive.

4. A surgical device according to claim 2, in which said flexible sheet is wider than said wings whereby to engage the skin of a patient beyond the outer ends of said wings.

5. A surgical device according to claim 2 in which said flexible sheet tapers symmetrically towards its free end from said wings.

6. A surgical device according to claim 5 in which the surface of said free end of said flexible sheet is non-adhesive.

7. A surgical device according to claim 1 in which said flexible sheet is formed with an opening to expose the location of the end of said cannula.

8. A surgical device according to claim 1 in which said cannula is in the form of a metal needle with a pointed end.

9. A surgical device according to claim 1, in which said cannula is of plastics material.

10. A surgical device according to claim 9, in which said cannula has a mount at its rear end and including a removable introducer needle fitted in said cannula and having a mount engaging said mount at the rear of said cannula.

11. A surgical device according to claim 2 in which said wings have surfaces which engage one another when said wings are folded to form a handle, said surfaces being formed with irregularities.

12. A surgical device according to claim 11, in which said surfaces of said wings are formed with corresponding ribs which are located so as to be alongside one another when said wings are folded symmetrically.

13. A surgical device according to claim 1 in which said at least one wing comprises two layers of plastics material secured together face-to-face with a length of said cannula between them.

14. A surgical device according to claim 13, having a pair of transverse wings, said wings comprising two sheets of plastics material with a portion of said flexible sheet fixed in position between said two sheets of plastics material.

15. A surgical device according to claim 14, in which said flexible sheet has tongues which are fixed in position between said two layers of plastics material, each said tongue having a cutaway portion.

16. A surgical device according to claim 2 in which said flexible sheet is removably fixed to said wings.

17. A surgical device according to claim 16, in which said flexible sheet has a layer of pressure-sensitive adhesive, said sheet being fixed to said wings by a portion of said layer of pressure-sensitive adhesive.

18. A surgical device according to claim 17 in which said flexible sheet has a pair of spaced tongues which carry said portion of said layer of pressure-sensitive adhesive.

19. A surgical device according to claim 18, including a cross-member connecting said tongues whereby to leave a small inspection opening.

20. In a surgical device of the kind comprising a cannula fitted with at least one laterally extending wing, the improvement which comprises a sheet of flexible material having a layer of pressure-sensitive adhesive and a removable barrier sheet covering such pressure sensitive adhesive, said sheet being wider than said at least one wing and being fixed to said at least one wing so as to extend rearwardly away from said at least one wing, said barrier sheet terminating to the rear of said at least one wing to define a fold line about which said sheet may be folded forwardly to cover said at least one wing with a marginal portion of said sheet extending both forwardly and rearwardly beyond the edges of said at least one wing and laterally beyond the sides of said at least one wing, whereby, when said barrier sheet is removed said marginal portion of said sheet engages the skin of a patient to hold said device in position.

21. A surgical device according to claim 20 wherein said at least one wing is formed from two layers of plastics material secured together face-to-face with a length of said cannula between them and said flexible sheet is formed with tongues which are fixed in position between said two layers of plastics material.

22. A surgical device according to claim 21 wherein said cannula is in the form of a metal needle with a pointed end and including a length of tubing fitted to said cannula, a portion of said tubing surrounding said cannula and lying between said two layers of plastics material, said tubing and said layers of plastics material being thermoplastic and being welded together to form a secure anchorage for said cannula.

* * * * *